United States Patent [19]

Umemura et al.

[11] 4,138,580
[45] Feb. 6, 1979

[54] PROCESS FOR PREPARING DIESTERS OF DICARBOXYLIC ACIDS

[75] Inventors: Sumio Umemura; Kanenobu Matsui; Yoshinari Ikeda; Katsuro Masunaga, all of Ube, Japan

[73] Assignee: Ube Industries, Ltd., Ube, Japan

[21] Appl. No.: 837,850

[22] Filed: Sep. 29, 1977

[30] Foreign Application Priority Data

Oct. 6, 1976 [JP] Japan .................................. 51/119403
Jul. 19, 1977 [JP] Japan .................................. 52/85565

[51] Int. Cl.$^2$ ............................................ C07C 67/38
[52] U.S. Cl. ..................................... 560/81; 560/114; 560/131; 560/139; 560/144; 560/146; 560/193; 560/198; 560/204
[58] Field of Search ................ 560/204, 81, 114, 193, 560/198, 131, 139, 144, 146

[56] References Cited

U.S. PATENT DOCUMENTS

| 3,397,226 | 8/1968 | Fenton ................................ 560/204 |
| 3,530,168 | 9/1970 | Biale ..................................... 260/486 |
| 3,625,995 | 12/1971 | Brattesoni ........................... 560/204 |
| 3,755,421 | 8/1973 | Fenton et al. ..................... 260/48 X |

FOREIGN PATENT DOCUMENTS

2161418 7/1972 Fed. Rep. of Germany.
2321180 11/1973 Fed. Rep. of Germany.
2512062 9/1975 Fed. Rep. of Germany.

OTHER PUBLICATIONS

J. Org. Chem. 37, No. 12, 2034–2035, (1972).
Derwent Abstract Jap. Pat. Provisional Publn. SHO-4-9-66619/1974.
Derwent Abstract Jap. Pat. Provisional Publn. SHO-4-9-116018/1974.

*Primary Examiner*—Jane S. Myers
*Attorney, Agent, or Firm*—Flynn & Frishauf

[57] ABSTRACT

A process for preparing a diester of a dicarboxylic acid having two more carbon atoms than the unsaturated hydrocarbon used as a starting material, which comprises subjecting an unsaturated hydrocarbon, carbon monoxide and an alcohol to reaction in the presence of a platinum group metal in combination with one or more compounds selected from the group consisting of nitric acid, a nitrogen oxide and an ester of nitrous acid.

16 Claims, No Drawings

PROCESS FOR PREPARING DIESTERS OF DICARBOXYLIC ACIDS

This invention relates to a novel process for preparing diesters of dicarboxylic acids.

More particularly, this invention relates to a process for preparing a diester of a dicarboxylic acid corresponding to the unsaturated hydrocarbon used as a starting material, namely, a diester of a dicarboxylic acid having two more carbon atoms than the unsaturated hydrocarbon used, which comprises subjecting an unsaturated hydrocarbon, carbon monoxide and an alcohol to reaction in the presence of a platinum group metal in combination with one or more compounds selected from the group consisting of nitric acid, a nitrogen oxide and an ester of nitrous acid, and introducing molecular oxygen into the reaction system as occasion demands.

According to this invention, a diester of succinic acid is obtained when ethylene is used as the unsaturated hydrocarbon, and diesters of dicarboxylic acids such as substituted succinic acids, substituted or unsubstituted maleic acid and cycloalkane dicarboxylic acids are obtained as the diester of a dicarboxylic acid when an unsaturated hydrocarbon other than ethylene is used as the starting material. For example, when propylene is used as the unsaturated hydrocarbon, a diester of methylsuccinic acid with a smaller amount of diesters of glutaric acid in some cases are obtained; when cyclohexene is used, a mixture of diesters of 1,2- and 1,3-cyclohexane dicarboxylic acids is obtained; and when acetylene is used, a diester of maleic acid is obtained.

A process for preparing a diester of a dicarboxylic acid having two more carbon atoms than the unsaturated hydrocarbon used as the starting material, which comprises subjecting an unsaturated hydrocarbon, carbon monoxide and an alcohol to reaction, and introducing molecular oxygen into the reaction system as occasion demands, is widely known, and various catalysts have been proposed for the reaction.

For example, U.S. Pat. No. 3,397,226 discloses an invention which employs as a catalyst a salt of a platinum group metal and a redox agent comprising a salt of a multivalent metal such as copper, iron, etc. However, it is taught that the reaction system should necessarily be kept substantially anhydrous, preferably by using a large amount of dehydrating agents such as isocyanates, diimides, orthoalkyl esters, etc., because this catalyst system brings about a decrease in the yield of the desired product, diester of dicarboxylic acid, due to water produced during the reaction and increased by-products such as carbon dioxide. Not only are the procedure and the control for maintaining an anhydrous reaction system very difficult and complicated according to this process, but also the dehydrating agent used cannot be reutilized since it is converted into an entirely different compound during the dehydration reaction. Accordingly, the cost for preparing a diester of a dicarboxylic acid becomes extremely high according to this conventional process. Furthermore, although it is suggested that a platinum group metal and a multivalent metal chloride are the most effective catalysts according to this conventional process, the corrosive action of the chloride is extremely strong and special apparatus of expensive material is required in practice.

A catalyst system in which an amino acid, a nickel compound and a metallic transition metal belonging to Group II, VII or VIII of the Periodic Table are used in combination as the third substance instead of a dehydrating agent has also been proposed for improvement of conventional catalyst systems. Although the water-resistance of these catalyst systems is enhanced, the yield and the selectivity of the desired product have not necessarily been increased to a satisfactory extent. Further, the conventional catalyst systems have problems in that the separation, recovery, regeneration, etc., of the expensive catalysts are complicated since a third substance is used in those catalyst systems and the catalyst systems are complicated because of their multi-components.

In view of these circumstances, we have made various studies to find an industrially superior catalyst system to those proposed conventionally, which is to be used in the process for preparing a diester of a dicarboxylic acid corresponding to the unsaturated hydrocarbon used as the starting material, which comprises subjecting an unsaturated hydrocarbon, carbon monoxide and an alcohol to reaction, with introduction of molecular oxygen as occasion demands. As a result of these studies, we have found that a diester of a dicarboxylic acid can be prepared industrially with high selectivity.

Namely, this invention relates to an industrially excellent process for preparing a diester of a dicarboxylic acid having two more carbon atoms than the unsaturated hydrocarbon used, which comprises subjecting an unsaturated hydrocarbon, carbon monoxide and an alcohol in the presence of a platinum group metal, in combination with one or more compounds selected from the group consisting of nitric acid, a nitrogen oxide and an ester of nitrous acid, and introducing molecular oxygen into the reaction system as occasion demands.

According to this invention, not only the yield and the selectivity of the desired diester of a dicarboxylic acid are increased in comparison with those of hitherto known processes, but also expensive dehydrating agents and complicated procedures and controls for keeping the reaction system anhydrous are unnecessary since our catalyst system is much less sensitive to water than the conventional catalysts. Further, the catalyst of this invention does not show any corrosive action against the apparatus and hence apparatus of a special material becomes unnecessary. Further, the catalyst system of this invention is simple, being composed of a platinum group metal and one or more compounds selected from the group consisting of nitric acid, a nitrogen oxide and an ester of nitrous acid. So, the procedures of separation, recovery and regeneration of the catalyst from the reaction system, and separation and obtaining of the desired product are simplified. Thus, the present process is industrially superior to hitherto known processes and is extremely significant industrially.

The present invention will be explained further in detail as follows.

As the unsaturated hydrocarbons used in this invention are aliphatic and alicyclic hydrocarbons having 2 to 20 carbon atoms such as ethylene, propylene, butene, pentene, hexene, heptene, octene, nonene, decene, undecene, dodecene, tridecene, tetradecene, pentadecene, hexadecene, heptadecene, octadecene, nonadecene, eicosene and their isomers, and cyclopentene, cyclohexene, cycloheptene, cyclooctene, indene, styrene, allyl benzene, allene, methylallene, butadiene, pentadiene, hexadiene, cyclopentadiene, etc.; and acetylene or its alkyl derivatives.

As the alcohols employed may be mentioned alkyl, cycloalkyl, aralkyl and acyl mono- or dialcohols. Particularly, aliphatic alcohols such as methanol, ethanol, propanol, butanol, pentanol, hexanol, heptanol, octanol, nonanol, decanol, ethylene glycol, diethylene glycol, propylene glycol, ethylene glycol monoalkyl ether, butane diol, etc., are preferred. Also employed are useful cyclic alcohols such as cyclopentanol, cyclohexanol, cycloheptanol, phenol, naphthol, cresol, cumenol, xylenol, benzyl alcohol, β-phenylethyl alcohol, etc.

As the platinum group metal used as the catalyst, while palladium is the most effective one, platinum, rhodium, ruthenium, iridium, osmium, etc., are also useful. In applying this invention industrially, it is convenient to use these platinum group metals in the form of a supported catalyst on such carriers as activated carbon, graphite, silica gel, alumina, silica alumina, diatomaceous earth, magnesium, pumice, molecular sieves, etc., in order to recover the platinum group metals or the desired product readily and to prevent the loss thereof.

These platinum group metals are used in an amount of from 0.00001 to 10% by weight, preferably from 0.0001 to 1.0% by weight of the reaction medium. Nitric acid is used in an amount of from 0.0001 to 10 moles per liter, preferably from 0.001 to 0.5 mole per liter of the reaction medium. Nitrogen oxides are used in an amount of from 0.1 to 100 mole %, preferably from 1 to 50 mole % of the unsaturated hydrocarbon used. Esters of nitrous acid are used in an amount of from 0.0001 to 10 moles, preferably from 0.001 to 1 mole per liter of the reaction medium. As the nitrogen oxide, nitrogen oxide is the most effective, but also useful is a nitrogen oxide such as dinitrogen trioxide, dinitrogen tetroxide, dinitrogen pentoxide, etc.

As the esters of nitrous acid used in this invention, all of the esters of nitrous acid with the above-mentioned alcohols used as a starting material in this invention are useful, but preferred industrially are such esters as, in particular, methyl nitrite, ethyl nitrite, propyl nitrite, butyl nitrite, pentyl nitrite, hexyl nitrite and heptyl nitrite. An ester of nitrous ester which is gaseous at room temperature, e.g., methyl nitrite, ethyl nitrite, etc., may effectively be used in the form of its solution in a corresponding alcohol.

The reaction of this invention may be carried out in the absence or presence of a solvent which does not inhibit the reaction. As such solvents may be exemplified ethers such as methylethyl ether, diethyl ether, dipropyl ether, dimethyl ether, dichloroethyl ether, ethylphenyl ether, diethylene glycol diethyl ether, triethylene glycol diethyl ether, etc.; esters such as methyl formate, ethyl formate, propyl formate, methyl acetate, ethyl acetate, propyl acetate, and esters of adipic acid, succinic acid, maleic acid, fumaric acid, propionic acid, acetoacetic acid, oxalic acid, benzoic acid, etc.; aromatic hydrocarbons such as benzene, nitrobenzene, chlorobenzene, toluene, etc.; alicyclic hydrocarbons such as cyclohexane, etc.

The reaction in this invention may proceed even under extremely mild conditions. The reaction temperature ranges from room temperature to 250° C., preferably from 50 to 150° C. The reaction pressure ranges from atmospheric pressure to 300 atm., preferably less than 200 atm. The molar ratio of carbon monoxide to unsaturated hydrocarbon ranges from 0.002 to 50, preferably from 0.01 to 5.

In this invention, molecular oxygen may be introduced into the reaction system to increase further the yield and the selectivity of the desired product. Molecular oxygen means oxygen gas, air and other oxygen-containing gases obtained by dilution of oxygen with an inert gas such as nitrogen. Usually, the more molecular oxygen introduced, the greater the yield of the desired product. However, molecular oxygen should be introduced only to such an extent that the gaseous mixture in the reactor is out of explosion limits.

EXAMPLE 1

An autoclave made of stainless steel, equipped with a magnetic rotary stirrer and having a capacity of 300 ml. was charged with 50 ml. of methanol, 50 ml. of dimethyl adipate as a solvent, 2 g. of palladium-on-activated carbon (2 wt. % Pd) and 10 mmoles of 61 wt. % nitric acid. After sealing, 36 atm. of ethylene and 24 atm. of carbon monoxide were pressured thereinto. Subsequently, after heating to 85° C., 3 atm. of oxygen were pressured therein twice and the reaction was carried out at 85° C. for 5 hours. After completion of the reaction, the reaction mixture was analyzed quantitatively by gas chromatography.

EXAMPLE 2

An experiment was run in the same manner as in Example 1, except that 18 atm. of carbon monoxide were pressured and the reaction was carried out for 3 hours.

EXAMPLE 3

An autoclave made of stainless steel, equipped with a magnetic rotary stirrer and having a capacity of 300 ml. was charged with 50 ml. of methanol, 50 ml. of dimethyl adipate, and 2 g. of palladium-on-activated carbon (2 wt. % Pd). After sealing, 45 atm. of ethylene and 15 atm. of carbon monoxide were pressured into the vessel. Subsequently, after heating at 85° C., the reaction was carried out for 3 hours while adding 30 mmoles of 61 wt. % nitric acid in 5 portions.

EXAMPLE 4

An experiment was run in the same manner as in Example 1, except that 20 mmoles of nitrogen dioxide were used in place of nitric acid, and the reaction was carried out for 3 hours.

EXAMPLE 5

An experiment was run in the same manner as in Example 1, except that 10 wt. % Pd on activated carbon was used as the catalyst, and the gas mixture used was composed of 45 atm. of ethylene and 15 atm. of carbon monoxide, and the reaction was carried out at 98° C. for 1 hour.

Comparative Example 1

An experiment was run in the same manner as in Example 1, except that nitric acid was not used.

Comparative Example 2

An autoclave made of stainless steel, equipped with a magnetic rotary stirrer, and having a capacity of 300 ml. was charged with 100 ml. of methanol, 0.94 mmole of palladium-black, 12.5 mmoles of copper nitrate and 0.24 mmole of nickel nitrate. After sealing, 36 atm. of ethylene and 24 atm. of carbon monoxide were pressured thereinto. Subsequently, after heating at 85° C., 3 atm.

of oxygen were twice pressured therein and the reaction was carried out at 85° C. for 3 hours.

Next, the results of the quantitative analyses by gas chromatography o the products conducted after completion of the reactios in Examples 1 to 5 and Comparative examples 1 and 2 are shown in following Table 1.

Table 1

|  |  | Amount of products (mmole) | |
|---|---|---|---|
|  |  | Desired product (Dimethyl succinate) | By-product (Dimethyl oxalate) |
| Examples | 1 | 43.6 | 8.8 |
|  | 2 | 30.8 | 9.7 |
|  | 3 | 19.2 | 6.0 |
|  | 4 | 15.2 | 17.1 |
|  | 5 | 13.9 | 1.9 |
| Comparative examples | 1 | 0.2 | 0.6 |
|  | 2 | 10.4 | 22.3* |

*In Comparative example 2, 4.0 mmoles of methyl β-methoxypropionate and 10.6 mmoles of dimethyl acetal of acetaldehyde, which were scarcely produced in Examples 1 to 5, were produced as by-products.

EXAMPLE 6

An autoclave made of stainless steel, equipped with a magnetic rotary stirrer and having a capacity of 300 ml., was charged with 80 ml. of methanol, 20 ml. of styrene, 2 g. of palladium-on-graphite (10 wt. % Pd) and 20 mmoles of 98 wt. % nitric acid. After sealing, 60 atm. of carbon monoxide were pressured thereinto. Subsequently, after heating at 85° C., 3 atm. of oxygen were twice pressured thereinto and the reaction was carried out at 85° C. for 3 hours.

After completion of the reaction, the reaction mixture was analyzed quantitatively by gas chromatography showing that 7.3 mmoles of dimethyl phenylsuccinate were produced.

EXAMPLE 7

An autoclave made of stainless steel, equipped with a magnetic rotary stirrer and having a capacity of 300 ml., was charged with 50 ml. of methanol, 50 ml. of dimethyl adipate as a solvent and 0.1 g. of palladium-on-activated-carbon (2 wt.% Pd). After sealing, the reaction was carried out under a reaction pressure of 30 atm. at a reaction temperature of 110° C. for 1 hour by passing a gas mixture composed of 90.4 vol.% of ethylene, 7.8 vol.% of carbon monoxide and 1.7 vol.% of oxygen through the vessel at a rate of 1.35 Nl./min. and feeding nitric acid dissolved in methanol at a rate of 90 mmoles/hour.

After completion of the reaction, the reaction mixture was analyzed quantitatively by gas chromatography, showing that 45.6 mmoles of dimethyl succinate were produced.

EXAMPLE 8

An autoclave made of stainless steel, equipped with a magnetic rotary stirrer and having a capacity of 300 ml., was charged with 50 ml. of ethanol, 50 ml. of diethyl adipate as a solvent and 1 g. of palladium-on-activated-carbon (2 wt.% Pd). After sealing, the reaction was carried out under a reaction pressure of 30 atm. at a reaction temperature of 90° C. for 1 hour while passing a gas mixture composed of 80.4 vol.% of ethylene, 13.1 vol.% of carbon monoxide and 6.5 vol.% of oxygen through the vessel at a rate of 1.2 Nl./min. and feeding nitric acid dissolved in ethanol at a rate of 100 mmoles/hour.

After completion of the reaction, the reaction mixture was analyzed quantitatively by gas chromatography, showing that 28.3 mmoles of diethyl succinate were produced.

EXAMPLE 9

An autoclave made of stainless steel, equipped with a magnetic rotary stirrer and having a capacity of 500 ml., was charged with 75 ml. of ethylene glycol, 75 ml. of methyl isobutyl ketone, 1 g. of palladium-on-activated-carbon (10 wt.% Pd) and 62 mmoles of 70 wt.% nitric acid.

After sealing, 35 atm. of ethylene and 20 atm. of carbon monoxide were pressured thereinto. Subsequently, after heating at 115° C., 3 atm. of oxygen were twice pressured thereinto and the reaction was carried out at 115° C. for 45 minutes.

After completion of the reaction, the reaction product was transesterified to n-butylesters by treatment with excess n-butanol and analyzed quantitatively by gas chromatography, showing that 7.2 mmoles of the diester of succinic acid were produced.

EXAMPLE 10

An experiment was run in the same manner as in Example 8, except that 150 ml. of ethylene glycol monomethyl ether were used instead of ethylene glycol, and methyl isobutyl ketone as a solvent was not used.

As a result of this, 25.8 mmoles of a diester of succinic acid were produced.

EXAMPLE 11

An autoclave made of stainless steel, equipped with a magnetic rotary stirrer and having a capacity of 300 ml., was charged with 30 ml. of 1,4-butanediol, 75 ml. of dioxane as a solvent, 1 g. of palladium-on-activated-carbon (10 wt.% Pd) and 41 mmoles of 98 wt.% nitric acid. After sealing, the reaction was carried out under a reaction pressure of 30 atm. at a reaction temperature of 105° C. for 1 hour by passing a gas mixture composed of 90.5 vol.% of ethylene, 4.6 vol.% of carbon monoxide and 4.9 vol.% of oxygen through the vessel at a rate of 0.59 Nl./min.

After completion of the reaction, the resulting reaction product was transesterified by treatment with methanol and the product obtained was analyzed quantitatively by gas chromatography, showing that 13.8 mmoles of the diester of succinic acid were produced.

EXAMPLE 12

An autoclave made of stainless steel, equipped with a magnetic rotary stirrer and having a capacity of 300 ml., was charged with 90 ml. of methanol, 10 ml. of cyclohexene, 2 g. of palladium-on-activated-carbon (5 wt.% Pd) and 25 mmoles of 98 wt.% nitric acid. After sealing, 40 atm. of carbon monoxide were pressured thereinto. Subsequently, after heating at 115° C., 3 atm. of oxygen were pressured thereinto four times and the reaction was carried out at 115° C. for 4 hours.

After completion of the reaction, the reaction mixture was analyzed quantitatively by gas chromatography, showing that 4.4 mmoles of dimethyl cis-1,2-cyclohexanedicarboxylate and 3.0 mmoles of dimethyl cis-1,3-cyclohexanedicarboxylate were produced.

EXAMPLE 13

An autoclave made of stainless steel, equipped with a magnetic rotary stirrer and having a capacity of 300 ml., was charged with 75 ml. of methanol, 2 g. of palladium-on-activated-carbon (10 wt.% Pd) and 53 mmoles of 61 wt.% nitric acid. After sealing, 34 g. of propylene were pressured thereinto, and subsequently carbon monoxide was pressured thereinto so as to make the total pressure 40 atm. Subsequently, after heating at 85° C., 4 atm. of oxygen were pressured thereinto 7 times and the reaction was carried out at 85° C. for 5 hours.

After completion of the reaction, the reaction mixture was analyzed quantitatively by gas chromatography to show that 20.6 mmoles of dimethyl methylsuccinate were produced.

EXAMPLE 14

An autoclave made of stainless steel, equipped with a magnetic rotary stirrer and having a capacity of 300 ml., was charged with 50 ml. of methanol, 50 ml. of dimethyl adipate as a solvent, 1 g. of palladium-on-activated-carbon (2 wt.% Pd) and 21 mmoles of n-butyl nitrite. After sealing, 40 atm. of a gas mixture composed of 91.6 vol.% of ethylene and 8.3 vol.% of carbon monoxide were pressured thereinto. Subsequently, when the pressure reached 50 atm. after raising the temperature to 105° C., 4 atm. of oxygen were pressured thereinto aand then the reaction was carried out at that temperature for 40 minutes.

EXAMPLE 15

An experiment was run in the same manner as in Example 14, except that 25 mmoles of ethyl nitrite dissolved in ethanol were used in place of n-butyl nitrite.

EXAMPLE 16

An experiment was run in the same manner as in Example 14, except that 100 ml. of n-butanol were used in place of methanol and dimethyl adipate as a solvent was not used.

EXAMPLE 17

An autoclave made of stainless steel, equipped with a magnetic rotary stirrer and having a capacity of 300 ml., was charged with 100 ml. of ethanol and 0.1 g. of palladium-on-activated-carbon (2 wt.% Pd). After sealing, 20 atm. of a gas mixture composed of 86.3 vol.% of ethylene, 10.3 vol.% of carbon monoxide and 3.2 vol.% of oxygen was pressured thereinto. Subsequently, after the pressure reached 30 atm. on raising the temperature to 145° C., the reaction was carried out for 1 hour while a solution of ethyl nitrite in ethanol was being supplied continuously, and 30 atm. of the above-mentioned gas mixture were being passed through the autoclave at a rate of 38 Nl./hour. The amount of ethyl nitrite supplied during the reaction was 60 mmoles.

EXAMPLE 18

An autoclave made of stainless steel, equipped with a magnetic rotary stirrer and having a capacity of 500 ml., was charged with 100 ml. of methanol, 50 ml. of dimethyl adipate as a solvent, 1 g. of palladium-on-activated-carbon (2 wt.% Pd) and 37.8 mmoles of n-butyl nitrite. After sealing, 23.3 g. of propylene were pressured thereinto and then carbon monoxide was pessured so as to make the total pressure 22 atm. Next, when the pressure reached 35 atm. after raising the temperature to 91° C., 2 atm. of oxygen were pressured thereinto and the reaction was carried out at that temperature for 5 hours. When a pressure decrease was not observed during the reaction, 2 atm. of oxygen were pressured twice into the reaction system.

EXAMPLE 19

An autoclave made of stainless steel, equipped with a magnetic rotary stirrer and having a capacity of 300 ml., was charged with 100 ml. of n-butanol and 1.5 g. of palladium-on-activated-carbon (2 wt.% Pd). After sealing, 45 atm. of a gas mixture composed of 81.2 vol.% of ethylene, 14.1 vol.% of carbon monoxide and 4.6 vol.% of oxygen were pressured thereinto.

Subsequently, after the temperature was raised to 118° C. and the pressure reached 60 atm., the reaction was carried out for 1 hour while supplying a solution of 7.9 g. of n-butyl nitrite dissolved in n-butanol and passing 60 atm. of the above-mentioned gas mixture through the vessel continuously. The amount of the n-butyl nitrite supplied during the reaction was 30.3 mmoles.

COMPARATIVE EXAMPLE 3

An autoclave made of stainless steel, equipped with a magnetic rotary stirrer and having a capacity of 300 ml., was charged with 1.13 mmoles of palladium chloride, 7.44 mmoles of cupric chloride, 50 ml. of methanol and 50 ml. of dimethyl adipate. After sealing, 24 atm. of carbon monoxide and 36 atm. of ethylene were pressured thereinto. Subsequently, when the pressure reached 61 atm. after raising the temperature to 100° C., 3 atm. of oxygen were pressured thereinto and the reaction was carried out at that temperature for 2.5 hours. When a pressure decrease was not observed, 3 atm. of oxygen were pressured 3 times thereinto.

Table 2 shows the results of quantitative analyses of Examples 14-19 and Comparative example 3 by gas chromatography conducted after completion of the reactions.

Table 2

| | | Amount of product (mmole) | |
|---|---|---|---|
| | | Desired product (Diester of succinic acid) | By-product (Diester of oxalic acid) |
| Examples | 14 | Dimethyl succinate 15.6 | Dimethyl oxalate 2.8 |
| | 15 | Dimethyl succinate 11.3 Diethyl succinate 2.2 | Dimethyl oxalate 2.0 |
| | 16 | Dibutyl succinate 8.1 | Dibutyl oxalate 3.9 |
| | 17 | Diethyl succinate 9.0 | Diethyl oxalate 0 |
| | 18 | Dimethyl methylsuccinate 28.2 | Dimethyl oxalate 6.0 |
| | 19 | Dibutyl succinate 37.1 | 0 |
| Comparative example 3* | | Dimethyl succinate 0.66 | 0 |

EXAMPLE 20

An autoclave made of stainless steel, equipped with a magnetic rotary stirrer and having a capacity of 300 ml., was charged with 100 ml. of ethanol and 2 g. of catalyst (2 wt.% palladium-on-activated-carbon). After sealing, a gas mixture composed of 86.3 vol.% of ethylene, 10.3 vol.% of carbon monoxide and 3.2 vol.% of oxygen was pressured into the autoclave (20 atm. at room temperature).

Then the autoclave was heated to 108° C., and the reaction conducted at that temperature for 1 hour by passing the gas mixture mentioned above through the reaction vessel at a rate of 0.6 Nl./min. and supplying a solution of nitric acid (42 mmoles) and ethyl nitrite (43 mmoles) in 25 ml. of ethanol.

After the reaction, the reaction products were analyzed quantitatively with gas chromatography, showing that 8.9 mmoles of diethyl succinate were produced.

EXAMPLE 21

An autoclave made of stainless steel, equipped with a magnetic rotary stirrer and having a capacity of 300 ml., was charged with 50 ml. of methanol, 50 ml. of dimethyl adipate, 21 mmoles of butyl nitrite and 1 g. of catalyst (2 wt.% palladium-on-activated-carbon). After sealing, a gas mixture composed of 91.6% of ethylene and 8.4% of carbon monoxide was pressured into the vessel to a pressure of 60 atm. The autoclave was kept at 105° C. for 1 hour, and the reaction mixture was analyzed with gas chromatography to show that 3.8 mmoles of dimethyl succinate and 1.7 mmoles of dimethyl oxalate were formed.

EXAMPLE 22

An autoclave made of stainless steel, equipped with a rotary magnetic stirrer and having a capacity of 300 ml., was charged with 50 ml. of methanol, 50 ml. of dimethyl adipate, 0.1 g. of catalyst (8 wt.% Pd — 2 wt.% Pt on activated carbon) and 36 mmoles of 98% nitric acid. After sealing, the vessel was charged with a gas mixture composed of 89.5 vol.% of ethylene, 7.5 vol.% of carbon monoxide and 2.7 vol.% of oxygen (20 atm. at room temperature). Then the autoclave was heated to 107° C., at which temperature the gas mixture mentioned above was passed through the vessel for 1 hour. The reaction mixture was analyzed with gas chromatography, showing that 21.5 mmoles of dimethyl succinate were produced.

EXAMPLE 23

An autoclave made of stainless steel, equipped with a magnetic rotary stirrer and having a capacity of 500 ml., was charged with 1.5 g. of 2 wt.% Pd on carbon, 38 mmoles of butyl nitrite, 75 ml. of n-butanol and 75 ml. of dibutyl adipate. After sealing the autoclave, 43 atm. of ethylene and 19 atm. of carbon monoxide were pressured thereinto and heated. The reaction was carried out at 105° C. for 1 hour without the addition of oxygen. After completion of the reaction, the reaction mixture was analyzed to show that 18.0 mmoles of dibutyl succinate and 4.3 mmoles of dibutyl oxalate were produced.

We claim:

1. A process for preparing a diester of a dicarboxylic acid having two more carbon atoms than the unsaturated hydrocarbon used as the starting material, which comprises subjecting an unsaturated hydrocarbon, carbon monoxide and an alcohol to reaction in the presence of a platinum group metal in combination with one or more compounds selected from the group consisting of nitric acid, a nitrogen oxide and an ester of nitrous acid, the amount of said nitric acid being from 0.0001 to 10 moles per liter of the reaction medium, the amount of said nitrogen oxide being from 0.1 to 100 mole % of the amount of the unsaturated hydrocarbon, and the amount of said ester of nitrous acid being from 0.0001 to 10 moles per liter of the reaction medium.

2. The process as claimed in claim 1, in which said reaction is carried out in the presence of molecular oxygen.

3. The process as claimed in claim 1, in which said platinum group metal is supported on a carrier.

4. The process as claimed in claim 1, in which said platinum group metal is palladium.

5. The process as claimed in claim 1, in which said unsaturated hydrocarbon is an aliphatic or alicyclic hydrocarbon having from 2 to 20 carbon atoms.

6. The process as claimed in claim 5, in which said unsaturated hydrocarbon is cyclohexene.

7. The process as claimed in claim 1, in which said unsaturated hydrocarbon is ethylene, propylene, acetylene or an alkyl derivative thereof.

8. The process as claimed in claim 1, in which said unsaturated hydrocarbon is styrene.

9. The process as claimed in claim 1, in which said platinum group metal is used in an amount of from 0.00001 to 10% by weight of the reaction medium.

10. The process as claimed in claim 9, in which said platinum group metal is used in an amount of from 0.0001 to 1.0% by weight of the reaction medium.

11. The process as claimed in claim 1, in which said reaction is carried out at a temperature of between room temperature and 250° C.

12. The process as claimed in claim 11, in which said reaction is carried out at a temperature of between 50° and 150° C.

13. The process as claimed in claim 1, in which said reaction is carried out under a pressure of between atmospheric pressure and 300 atm.

14. The process as claimed in claim 12, in which said reaction is carried out under a pressure of between 10 and 200 atm.

15. The process as claimed in claim 1, in which said carbon monoxide and unsaturated hydrocarbon are used in a molar ratio 0.002–50.

16. The process as claimed in claim 15, in which said carbon monoxide and unsaturated hydrocarbon are used in a molar ratio of 0.01–5.

* * * * *

UNITED STATES PATENT AND TRADEMARK OFFICE
CERTIFICATE OF CORRECTION

PATENT NO. : 4,138,580
DATED : February 6, 1979
INVENTOR(S) : SUMIO UMEMURA et al It is certified that error appears in the above-identified patent and that said Letters Patent are hereby corrected as shown below:

Column 5, line 4: rewrite "o" as ---of---.

Column 5, line 5: rewrite "reactios" as ---reactions---.

Column 8, line 51 (after Table 2), insert the following:
---*In Comparative example 3, it was found that 13.1 moles of a formate (methyl formate) and a large amount of dimethyl acetal of acetaldehyde and carbon dioxide, which were scarcely produced in Examples 14-19, were produced as by-products.---.

Signed and Sealed this

Thirtieth Day of October 1979

[SEAL]

Attest:

RUTH C. MASON
Attesting Officer

LUTRELLE F. PARKER
Acting Commissioner of Patents and Trademarks